US006344586B1

(12) United States Patent
Ichihashi et al.

(10) Patent No.: US 6,344,586 B1
(45) Date of Patent: Feb. 5, 2002

(54) PROCESS FOR PRODUCING ADIPIC ACID

(75) Inventors: Hiroshi Ichihashi; Kazuhide Tanaka, both of Niihama (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 09/744,805

(22) PCT Filed: Jul. 23, 1999

(86) PCT No.: PCT/JP99/03951

§ 371 Date: Jan. 30, 2001

§ 102(e) Date: Jan. 30, 2001

(87) PCT Pub. No.: WO00/06528

PCT Pub. Date: Feb. 10, 2000

(30) Foreign Application Priority Data

Jul. 30, 1998 (JP) ............................................. 10-215513

(51) Int. Cl.$^7$ ................................................. C07C 55/00
(52) U.S. Cl. ..................................................... 562/590
(58) Field of Search ................................ 562/590, 543; 549/267

(56) References Cited

U.S. PATENT DOCUMENTS

| 3,277,168 A | * | 10/1966 | Koenig | ....................... 260/535 |
|---|---|---|---|---|
| 3,597,530 A | * | 8/1971 | Wegerich et al. | ............. 203/29 |
| 3,649,685 A | * | 3/1972 | Ishimoto et al. | ............ 260/533 |
| 4,032,569 A | * | 6/1977 | Onopchenko et al. | ...... 260/533 |
| 4,902,827 A | * | 2/1990 | Steinmetz et al. | .......... 562/543 |
| 5,969,194 A | | 10/1999 | Hara et al. | .................. 568/700 |

FOREIGN PATENT DOCUMENTS

| FR | 1512534 | 2/1968 |
|---|---|---|
| JP | 54-92913 | 7/1979 |
| JP | 4-356440 | 12/1992 |
| JP | 8-502247 | 3/1996 |

* cited by examiner

*Primary Examiner*—Gary Geist
*Assistant Examiner*—Zachary C. Tucker
(74) *Attorney, Agent, or Firm*—Sughrue Mion, PLLC

(57) ABSTRACT

A process for producing adipic acid is provided which comprises a step of oxidizing hydroxycaproic acid and/or ε-caprolactone with oxygen or oxygen-containing gas using a metal in the platinum group as a catalyst. According to the process, adipic acid is produced without using nitric acid, which becomes the main factor responsible for the by-production of nitrogen oxides, and without using any particularly high-pressure conditions.

11 Claims, No Drawings

PROCESS FOR PRODUCING ADIPIC ACID

TECHNICAL FIELD OF THE INVENTION

The present invention relates to a process for the production of adipic acid, and particularly to a process for producing adipic acid by oxidizing hydroxycaproic acid or ε-caprolactone using a specific catalyst.

BACKGROUND OF THE INVENTION

Adipic acid is used as a raw material of various organic chemical products such as nylon 6,6, a raw material of urethane (1,6-hexamethylendiol) and plasticizers.

Hitherto, adipic acid has generally been produced by the oxidation, with nitric acid, of a mixture of cyclohexanol and cyclohexanone, both of which are obtained by the liquid-phase oxidation of cyclohexane, the mixture being henceforth referred to as KA oil. Although the production process by the oxidation of KA oil with nitric acid provides adipic acid in a high yield, it has a problem about the disposal of nitrogen oxides since it produces as by-products nitrogen oxides such as nitrous oxide $N_2O$, which has much effect on global warming. For example, the oxidation of cyclohexanol with nitric acid produces nitrous oxide as by-products in accordance with the following formula:

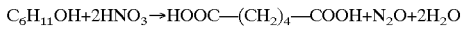
$C_6H_{11}OH+2HNO_3 \rightarrow HOOC-(CH_2)_4-COOH+N_2O+2H_2O$

Processes of directly oxidizing cyclohexanol or cyclohexanone with air in place of nitric acid, which have been under development, are not very satisfactory in the yield of the product.

Moreover, a process for obtaining adipic acid by carbonylation of butadiene with carbon monoxide has been under development, but it is problematic in that it needs reaction conditions including high pressure or it can not achieve the sufficient yield of the product.

Incidentally, cyclohexanone and cyclohexanol are now produced by liquid-phase oxidation of cyclohexane in an industrial scale. The production process, however, gives cyclohexanone and cyclohexanol in a total yield of from about 70% to about 90% and also produces a by-product in a total yield of from about 10% to about 30%, which contains adipic acid, hydroxycaproic acid, ε-caprolactone and the like in relatively high concentrations. For example, when cyclohexane is oxidized with air using a cobalt salt as a catalyst, the acid waste water provided as a by-product contains 5% by weight to 15% by weight of adipic acid, 5% by weight to 10% by weight of hydroxycaproic acid, 0.1% by weight to 0.5% by weight of ε-caprolactone and 0.1% by weight to 0.5% by weight of adipic ester. Although recovering adipic acid from the by-produced acid waste water is considered to be desirable from the viewpoints of efficiency of resources utilization and reduction of environmental load, hydroxycaproic acid and ε-caprolactone are disposed by a method of incineration or the like with little recovery due to their little demand.

SUMMARY OF THE INVENTION

Under such circumstances, the present inventors diligently studied for the purpose of finding a process for producing adipic acid without using nitric acid as a raw material, which becomes the main factor responsible for the by-production of nitrogen oxides, and without using any particularly high-pressure conditions. As a result, the present inventors have found that when hydroxycaproic acid and/or ε-caprolactone is oxidized using a specific catalyst, adipic acid can be produced efficiently with no nitric acid or no particularly high-pressure conditions and also found that by this process, hydroxycaproic acid, ε-caprolactone and the like obtained as by-products and previously, mainly incinerated to be disposed can be used effectively. Also, the present inventors have found that such a process for producing adipic acid satisfies all the foregoing objects by oxidizing even the hydroxycaproic acid, ε-caprolactone and the like, that are the by-products in producing cyclohexanone and cyclohexanol by the oxidation of cyclohexane, with the specific catalyst. After such findings, the present inventors have completed the present invention.

Thus, the present invention provides a process for producing adipic acid which comprises a step of oxidizing hydroxycaproic acid and/or ε-caprolactone with oxygen or oxygen-containing gas using a metal in the platinum group as a catalyst.

DETAILED DESCRIPTION OF THE INVENTION

The present invention uses hydroxycaproic acid and/or ε-caprolactone as raw materials.

In a state of an aqueous solution, ε-caprolactone is hydrolyzed to form hydroxycaproic acid and hydroxycaproic acid is cyclodehydrated to form ε-caprolactone so that both compounds gradually go toward an equilibrium state thereof in an aqueous solution with time. In the present invention, as a raw material may be used either hydroxycaproic acid alone or ε-caprolactone alone. However, whichever compound is used, a mixture of both compounds will be substantially used because of such an equilibrium when water is used as a solvent.

The hydroxycaproic acid and/or ε-caprolactone to be used in the present invention may be those obtained by any method and are not particularly limited. Examples thereof include hydroxycaproic acid and ε-caprolactone, that are produced as by-products during the production of cyclohexanone and cyclohexanol by air oxidation of cyclohexane. In this case, adipic acid can also be produced from esters of hydroxycaproic acid contained together as impurities. The hydroxycaproic acid to be used in the present invention includes esters of hydroxycaproic acid. Examples of the esters of hydroxycaproic acid include esters produced by the dehydration of an acid such as acetic acid, oxalic acid, caproic acid or adipic acid with hyroxycaproic acid, an ester produced by the dehydration condensation of cyclohexanol and hydroxycaproic acid, and an ester produced by the dehydration condensation between two hydroxycaproic acid molecules at their carboxyl and hydroxyl groups.

In the present invention, adipic acid is produced by oxidizing a raw material, i.e. ε-caprolactone, hyroxycaproic acid or a mixture thereof with oxygen or an oxygen-containing gas in the presence of a catalyst comprising a metal in the platinum group, preferably in an aqueous solution state. In the case that the raw material is used in an aqueous solution state, the concentrations of the hydroxycaproic acid and/or ε-caprolactone in the aqueous solution may be from about 1% by weight to about 40% by weight, preferably from about 2% by weight to about 20% by weight.

As a catalyst, a metal selected from metals in the platinum group is used. Specifically, examples of the metal in the platinum group include platinum, palladium, rhodium and ruthenium and the like. At least one metal selected from these metals is applied. The catalyst may be used with being supported on a carrier or used as it is. For example, metallic fine particles such as platinum black or palladium black may be used as they are. Examples of the carrier include activated carbon, silica, alumina, titania and zeolite. Among them, activated carbon is particularly preferred. When the catalyst is used with being supported on a carrier, the supporting ratio of a metal component to the carrier may be from about 0.1% by weight to about 8% by weight, preferably from about 0.2% by weight to about 4% by weight.

An amount of the oxygen to be used in the oxidation may be about 1 time or more, preferably in the range of from about 2 times to about 20 times, in molar ratio based on the sum of ε-caprolactone and hydroxycaproic acid.

Specifically, the present invention may be conducted by a method in which the raw materials, i.e. ε-caprolactone and/or hydroxycaproic acid, are fed in a form of an aqueous solution into a tank-type reactor, a catalyst is added and then oxygen gas or an oxygen-containing gas such as air is fed thereto under stirring. Alternatively, it may be conducted by a method in which a reactor is packed with a catalyst supported on activated carbon or the like and an aqueous solution of ε-caprolactone and/or hydroxycaproic acid is fed together with an oxygen molecule-containing gas to the catalyst layer.

In the case of conducting the reaction in the tank-type reactor, the amount of catalyst to be used in the reaction may fall within the range of from about 0.1% to about 200%, preferably within the range of from about 0.1% to about 100%, in weight ratio based on ε-caprolactone and/or hydroxycaproic acid. When the reaction is conducted in a flow system using a packed layer-type reactor, ε-caprolactone and/or hydroxycaproic acid are fed to the catalyst layer at a space velocity (that is the weight of the raw materials fed per unit time per unit catalyst weight; WHSV) of from about 0.02 $h^{-1}$ to about 5 $h^{-1}$, preferably from about 0.05 $h^{-1}$ to about 2 $h^{-1}$.

The reaction temperature may fall within the range of from about 80° C. to about 220° C., preferably within the range of from about 100° C. to about 180° C. When the reaction temperature is lower than about 80° C., reaction speed achieved is not satisfactory. When it exceeds about 220° C., selectivity to adipic acid tends to decrease.

The adipic acid obtained can be recovered from the reaction mixture by crystallization. Examples of the crystallization method include a method of cooling the reaction mixture to crystallize adipic acid and a method of vaporizing water to concentrate adipic acid so as to crystallize it.

As described in detail above, according to the present invention, adipic acid can be produced without generation of nitrogen oxides. Moreover, when hydroxycaproic acid and/or ε-caprolactone are used as raw materials, both of which are produced as by-products in the production of cyclohexanone and cyclohexanol by oxidizing cyclohexane, the by-products can be utilized effectively. Thus, the invention has extremely great industrial value.

EXAMPLES

The present invention is illustrated further in detail below by reference to examples, but these examples are merely some embodiments of the present invention and the invention is not limited by the examples. Unless otherwise stated, all percentage unit (%) used in the examples indicate percent by mole unit (mol %).

Example 1

Into a 100 ml-capacity stainless steel autoclave, 0.4 g of ε-caprolactone and 19.6 g of water were added and 40 mg of palladium black was added as a catalyst. After that, the gas in the autoclave was replaced with oxygen gas under the conditions of ordinary temperature and pressure and the autoclave was then sealed. The autoclave was subsequently heated up to 120° C. under stirring and kept at the same temperature for 4 hours. The autoclave was then cooled down to room temperature and the reaction mixture was analyzed by means of gas chromatography.

The conversion of ε-caprolactone was found to be 99% and the yield of adipic acid was found to be 44% based on the ε-caprolactone used as the raw material. In the reaction mixture, hydroxycaproic acid was also present and the amount thereof corresponded to a yield of 46% based on the ε-caprolactone used as the raw material.

Example 2

A reaction was carried out in the same manner as in Example 1 except that a reaction time was changed to 2 hours. An analysis revealed that the conversion of ε-caprolactone was 99% and the yields of adipic acid and hydroxycaproic acid were 20% and 73%, respectively, based on the ε-caprolactone used as the raw material.

Example 3

A reaction was carried out in the same manner as in Example 1 except that a reaction time was changed to 1 hour. An analysis revealed that the conversion of ε-caprolactone was 99% and the yields of adipic acid and hydroxycaproic acid were 12% and 84%, respectively, based on the ε-caprolactone used as the raw material.

Example 4

In the same manner as in Example 1, into a 100 ml-capacity stainless steel autoclave, 0.4 g of ε-caprolactone and 19.6 g of water were added and 40 mg of palladium black was added as a catalyst. After that, the gas in the autoclave was replaced with oxygen gas under the conditions of ordinary temperature and pressure and the autoclave was then sealed. A reaction was carried out by keeping the autoclave at 120° C. for 4 hours under stirring. After that, the autoclave was cooled down to room temperature, and then the gas in the autoclave was replaced with oxygen gas to seal the autoclave again. Then, the temperature in the autoclave was elevated again and kept at 120° C. for 4 hours under stirring, so that the reaction was continued. After cooling down to room temperature, the reaction mixture was analyzed by means of gas chromatography.

The conversion of ε-caprolactone was found to be 100% and the yields of adipic acid and hydroxycaproic acid were found to be 82% and 9%, respectively, based on the ε-caprolactone used as the raw material.

The results of from Examples 1 to 4 are shown in Table 1. It is clear from Table 1 that ε-caprolactone is changed to hydroxycaproic acid first, and then adipic acid is produced.

TABLE 1

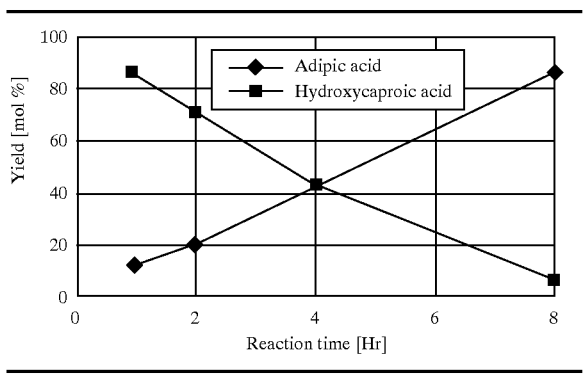

Comparative Example 1

To 120 ml of a 30%-by-weight aqueous nitric acid solution that contained 8 mmol of palladium nitrate and 2.4 mmol of tellurium dioxide therein, 40 g of crushed palm shell activated carbon was added, and the resulting mixture was heated and refluxed for 4 hours. After that, the solvent in the mixture was distilled out under reduced pressure by means of an evaporator, so that the reaction mixture was dried up. The resulting dried cake was left at 150° C. in a nitrogen flow for 2 hours to be completely dried, and then kept at 200° C. for 2 hours and at 400° C. for another 1 hour in a 1.5-L/minute flow of a nitrogen gas saturated with methanol at room temperature, to be subjected to reduction. Thus, an activated carbon-supported catalyst containing 2% by weight of palladium metal and 0.8% by weight of tellurium metal was produced.

Example 5

A reaction was carried out in the same manner as in Example 1 except that 0.4 g of activated carbon-supported catalyst prepared in Comparative Example 1 was used in place of palladium black used as a catalyst in Example 1. An analysis revealed that the yields of adipic acid and hydroxycaproic acid were 23% and 63%, respectively, based on the ε-caprolactone used as the raw material.

Example 6

A reaction was carried out in the same manner as in Example 1 except that 0.4 g of carbon beads supporting 1% by weight of platinum was used in place of palladium black used as a catalyst in Example 1. An analysis revealed that the yields of adipic acid and hydroxycaproic acid were 26% and 57%, respectively, based on the ε-caprolactone used as the raw material.

Example 7

A reaction was carried out in the same manner as in Example 1 except that 0.4 g of carbon powder supporting 2% by weight of ruthenium was used in place of palladium black used as a catalyst in Example 1. An analysis revealed that the yields of adipic acid and hydroxycaproic acid were 16% and 71%, respectively, based on the ε-caprolactone used as the raw material.

Example 8

A reaction was carried out in the same manner as in Example 1 except that 0.4 g of carbon powder supporting 2% by weight of palladium was used in place of palladium black used as a catalyst in Example 1. An analysis revealed that the yields of adipic acid and hydroxycaproic acid were 43% and 44%, respectively, based on the ε-caprolactone used as the raw material.

Example 9

A reaction was carried out in the same manner as in Example 1 except that 0.4 g of silica spheres (1.5 mmφ) supporting 2% by weight of palladium was used in place of palladium black used as a catalyst in Example 1. An analysis revealed that the yields of adipic acid and hydroxycaproic acid were 29% and 71%, respectively, based on the ε-caprolactone used as the raw material.

Example 10

A reaction was carried out in the same manner as in Example 1 except that 0.4 g of carbon powder containing palladium metal (2% by weight) and antimony metal (0.2% by weight) was used in place of palladium black used as a catalyst in Example 1. An analysis revealed that the yields of adipic acid and hydroxycaproic acid were 11% and 29%, respectively, based on the ε-caprolactone used as the raw material.

Example 11

Cyclohexanone and cyclohexanol were produced by the liquid-phase oxidization of cyclohexane. From the resulting reaction mixture, were taken out cyclohexanone, cyclohexanol and unreacted cyclohexane to leave an acid waste water. In the acid waste water, adipic acid, hydroxycaproic acid, glutaric acid, ε-caprolactone, adipic ester, hydroxycaproic ester and the like were contained.

A reaction was carried out in the same manner as in Example 1 except that 20 g of a solution obtained by diluting the above acid waste water five fold was used in place of 0.4 g of ε-caprolactone and 19.6 g of water in Example 1.

An analysis revealed that the conversion of hydroxycaproic acid was 10% and the yield of adipic acid was 15%, both based on the hydroxycaproic acid in the acid waste water used as the raw material. It seems that the yield of adipic acid is larger than the conversion of hydroxycaproic acid since adipic acid was also produced from the ester compounds of adipic acid and hydroxycaproic acid contained in the acid waste water, which was the raw material.

Example 12

A reaction was carried out in the same manner as in Example 11 except that the reaction temperature was kept at 120° C. for 8 hours in place of being kept at 120° C. for 4 hours. An analysis revealed that the conversion of hydroxycaproic acid was 23% and the yield of adipic acid was 35%, both based on the hydroxycaproic acid in the acid waste water used as the raw material. It seems that the yield of adipic acid is larger than the conversion of hydroxycaproic acid since adipic acid was also produced from the ester compounds of adipic acid and hydroxycaproic acid contained in the acid waste water, which was the raw material.

Example 13

A packed layer-type stainless steel reactor having an inner diameter of 15.7 mmφ was packed with 15 g of a catalyst in which palladium was supported (2% by weight) on a carbon-bead carrier, and the inner pressure of the reactor was elevated up to 5 MPa with air. After that, from the bottom of the reactor were supplied an aqueous solution containing 4.3% by weight of ε-caprolactone at a rate of 48 g/hr and air at a rate of 18 NL/hr, so that the reaction was carried out in a flow system while heating the reactor by means of a band heater. Although a distribution occurred in the temperature of the catalyst layer since the reaction was exothermic, the temperature at the place where the highest temperature was detected was kept at 140° C. throughout the reaction. The resulting reaction mixture was collected and analyzed with ion chromatography. The yield of adipic acid was found to be 64% based on the ε-caprolactone used as the raw material. In the reaction mixture, hydroxycaproic acid was present in an amount corresponding to a yield of 11% based on the ε-caprolactone used as the raw material.

Example 14

A reaction was carried out in the same manner as in Example 13 except that an aqueous solution containing 2.15% by weight of ε-caprolactone was supplied at a rate of 96 g/hr in place of suppying the aqueous solution containing 4.3% by weight of ε-caprolactone at a rate of 48 g/hr. The reaction mixture was collected and analyzed. The yields of adipic acid and hydroxycaproic acid were 64% and 12%, respectively, both based on the ε-caprolactone used as the raw material.

Example 15

A reaction was carried out in the same manner as in Example 14 except that the highest temperature of the catalyst layer was changed from 140° C. to 146° C. An analysis revealed that the yields of adipic acid and hydroxycaproic acid were 70% and 8%, respectively, both based on the ε-caprolactone used as the raw material.

Example 16

Cyclohexanone and cyclohexanol were produced by the liquid-phase oxidization of cyclohexane. From the resulting reaction mixture, were taken out cyclohexanone, cyclohexanol and unreacted cyclohexane to leave an acid waste water. In the acid waste water, adipic acid, hydroxycaproic acid, glutaric acid, ε-caprolactone, adipic ester, hydroxycaproic ester and the like were contained.

A reaction was carried out in the same manner as in Example 13 except that 30 g of a catalyst in which palladium was supported (2% by weight) on carbon beads carrier in place of packing 15 g of the catalyst, that a solution obtained by diluting the above acid waste water three fold was supplied at a rate of 27 g/hr in place of supplying the aqueous solution containing 4.3% by weight of ε-caprolactone at a rate of 48 g/hr and that the highest temperature of the catalyst layer during the reaction was changed from 140° C. to 131° C. An analysis revealed that the conversion of hydroxycaproic acid was 48% and the yield of adipic acid was 47%, both based on the hydroxycaproic acid in the acid waste water used as the raw material.

Example 17

A reaction was carried out in the same manner as in Example 16 except that the highest temperature of the catalyst layer was changed to 133° C. and that as a feeding solution, namely as a raw material, was used a solution obtained by diluting three fold with water, a filtrate which was obtained by the steps of concentrating the acid waste water given in producing cyclohexanone and cyclohexanol by the liquid-phase oxidation of cyclohexane, conducting crystallization and recovering crude adipic acid therefrom. An analysis revealed that the conversion of hydroxycaproic acid was 27% and the yield of adipic acid was 38%, both based on the hydroxycaproic acid in the filtrate used as the raw material. It seems that the yield of adipic acid is larger than the conversion of hydroxycaproic acid since adipic acid was also produced from the ester compounds of adipic acid and hydroxycaproic acid contained in the filtrate, which was the raw material.

What is claimed is:

1. A process for producing adipic acid which comprises a step of oxidizing hydroxycaproic acid and/or ε-caprolactone with oxygen or oxygen-containing gas using a metal in the platinum group as a catalyst.

2. The process for producing adipic acid according to claim 1 wherein the metal in the platinum group is at least one metal selected from platinum, palladium, rhodium and ruthenium.

3. The process for producing adipic acid according to claim 1 wherein the metal in the platinum group is supported on a carrier.

4. The process for producing adipic acid according to claim 3 wherein the carrier is activated carbon.

5. The process for producing adipic acid according to any one of claims 1, 2, 3 or 4 wherein water is allowed to be present in the reaction system.

6. The process for producing adipic acid according to any one of claims 1, 2, 3 or 4 wherein the hydroxycaproic acid and/or ε-caprolactone are dissolved in water.

7. A process for producing adipic acid which comprises the steps of:
(i) oxidizing cyclohexane in a liquid phase to obtain a reaction mixture containing cyclohexanone and cyclohexanol,
(ii) taking out cyclohexane, cyclohexanone and cyclohexanol from the reaction mixture to obtain an acid waste water containing hydroxycaproic acid and/or ε-caprolactone, and
(iii) oxidizing the hydroxycaproic acid and/or ε-caprolactone in the acid waste water with oxygen or an oxygen-containing gas using a metal in the platinum group as a catalyst.

8. The process for producing adipic acid according to claim 2 wherein the metal in the platinum group is supported on a carrier.

9. The process for producing adipic acid according to claim 8 wherein the carrier is activated carbon.

10. The process for producing adipic acid according to claim 8 or 9 wherein water is allowed to be present in the reaction system.

11. The process for producing adipic acid according to claim 8 or 9 wherein the hydroxycaproic acid and/or ε-caprolactone are dissolved in water.

* * * * *